United States Patent [19]

Jacobs, III et al.

[11] 4,312,988

[45] Jan. 26, 1982

[54] SYNTHESIS OF HYDROXY FUNCTIONAL MELAMINE DERIVATIVES

[75] Inventors: William Jacobs, III, Bridgeport; James C. Goebel, New Canaan, both of Conn.

[73] Assignee: American Cyanamid Company, Stamford, Conn.

[21] Appl. No.: 205,119

[22] Filed: Nov. 10, 1980

[51] Int. Cl.$^3$ .................. C07D 251/70; C07D 251/18; C07D 251/22

[52] U.S. Cl. .................................. 544/196; 544/197; 544/205; 544/206; 544/194; 544/211

[58] Field of Search ............... 544/196, 197, 205, 206, 544/194, 211

[56] References Cited

U.S. PATENT DOCUMENTS 2,328,961 9/1943 D'Alelio et al. ..................... 544/196
2,393,755 1/1946 D'Alelio ............................. 544/197
2,723,244 11/1955 Joyce et al. ........................ 544/206

*Primary Examiner*—John M. Ford
*Attorney, Agent, or Firm*—Bruce F. Jacobs

[57] ABSTRACT

The amount of isomelamine impurities formed in the reaction of melamine and an alkanolamine may be reduced by using isopropanolamine as the alkanolamine.

4 Claims, No Drawings

SYNTHESIS OF HYDROXY FUNCTIONAL MELAMINE DERIVATIVES

This invention relates to the reaction of a melamine compound and an alkanolamine whereby the amount of isomelamine impurity is greatly reduced. Specifically, it relates to the use of isopropanolamine (1-amino-2- propanol) as the alkanolamine.

The prior art, such as U.S. Pat. Nos. 2,328,961, 2,393,755, 2,467,523 and 2,723,244, suggests the reaction of melamine with amines such as alkanolamines but makes no distinction between straight-chain alkanolamines and branched-chain ones, and it further makes no mention of the isomelamine impurity problem.

It has now been discovered that by using isopropanolamine in the reaction, the isomelamine content may be drastically reduced.

The reaction of melamine with an alkanolamine is an amine-displacement reaction according to:

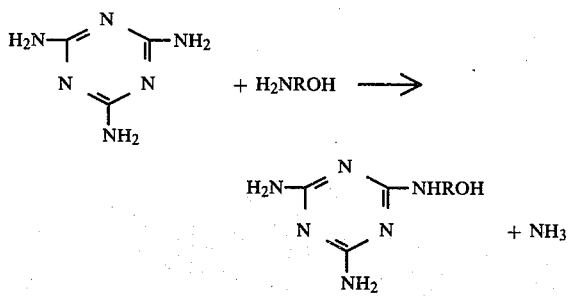

However, when an alkanolamine such as ethanolamine is used a substantial amount of cyclization occurs by attack of the ring N on the —CH$_2$OH group displacing water and forming an isomelamine of the formula

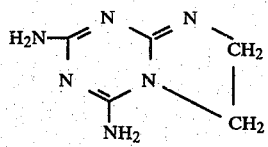

Correspondingly, when two or three moles of ethanolamine are reacted with one mole of melamine, the isomelamines of the following formulae are produced:

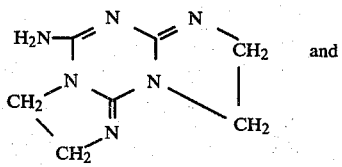

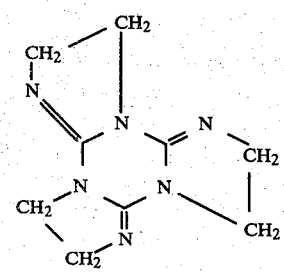

A similar cyclization occurs when propanolamine is substituted for the ethanolamine in the above reaction.

These isomelamine impurities are undesirable because their formation involves a loss of —OH functionality, and results in a much darker product.

Accordingly, it is an object of the present invention to reduce the formation of isomelamine impurities in the reaction of a melamine and an alkanolamine.

The amino-s-triazine compounds useful herein are those of the formula

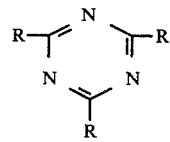

wherein each R is selected from alkyl (C$_1$-C$_{20}$), cycloalkyl (C$_5$C$_8$), aryl (C$_6$-C$_{12}$), NH$_2$, and NHR' wherein R' is selected from alkyl (C$_1$-C$_{20}$), cycloalkyl (C$_5$-C$_8$), and aryl (C$_6$-C$_{12}$), and at least one R is NH$_2$. Preferably at least two R's are NH$_2$ and most preferably all three R's are NH$_2$ and the compound is melamine per se.

By "isopropanolamine" herein is meant compounds of the formula

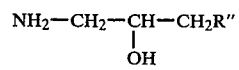

wherein R'' is hydrogen, alkyl (C$_1$-C$_{20}$), or phenyl. It is used in amounts of about one to three moles per mole of melamine compound.

In addition to the melamine and the isopropanolamine, the reaction vessel may also contain other reactants as desired. Examples of such include alkyl or aryl amines or ether amines or diamines like 1,6-hexamethylene diamine, 1,4-butylene diamine, 1,2- ethylene diamine, octylamine, stearylamine, laurylamine, phenylamine, naphthylamine, and polyethylene amines.

The reaction occurs under standard conditions for amine-melamine reactions, i.e. at a temperature of about 100° to 250° C., preferably 150° to 200° C., in the presence of an acidic catalyst, and optionally with suitable solvents.

Suitable acidic atalysts include hydrogen chloride, sulfuric acid, p-toluene sulfonic acid, phosphoric acid, ammonium chloride, and the like.

The resultant products have been found to be useful in the production of urethanes, either as made or after subsequent reaction with an alkylene oxide, as well as for laminating resins, molding compounds, and as crosslinking agents after reaction with formaldehyde.

In the following non-limiting examples all parts and percents are by weight unless otherwise specified.

EXAMPLE 1

To a suitable reactor is added 252 grams (2.0 moles) of melamine, 480 grams (6.4 moles) of 1-amino-2-propanol (1,2-PA), 314 grams of ethylene glycol (30% by weight), and 19.8 grams of ammonium chloride catalyst (0.35 moles per kilogram of reaction mixture). Under nitrogen the reaction mixture is stirred, brought to reflux, and followed by titration of the amines with 0.1N HCl using phenol red indicator. Infrared analysis at 75% conversion shows a total absence of isomelamine products, and at 95% conversion shows about 13% isomelamine.

Cooling the reaction to 100° C., neutralizing the acid catalyst present with an equivalent amount of sodium hydroxide, followed by removal of the excess 1,2-PA and ethylene glycol solvent under vacuum at 150° to 180° produces a product containing a maximum of 40% isomelamine compounds.

COMPARATIVE EXAMPLE A

The procedure of Example 1 is repeated except using 6.4 moles (390.4 grams) of ethanolamine in place of the 1,2-PA. The isomelamine content at various levels of conversion is:

| % Conversion | % Isomelamine |
|---|---|
| 82 | 20 |
| 95 | 50 |
| 99 | 100 |

EXAMPLE 2

A melamine resin is prepared having the average composition of two parts melamine one part, 1,6-hexamethylene diamine (HMDA) and four parts 1-amino-2-propanol (1,2-PA).

Into a suitably designed reactor is placed 94.5 grams (0.75 moles) of melamine, 43.5 grams (0.375 moles) of HMDA, 140.83 grams (1.875 moles) of 1,2-PA, 5.22 grams of ammonium chloride catalyst (0.35 moles of catalyst per kilogram of reactants), and 71.01 g of ethylene glycol (25% by weight). The reactor is purged with nitrogen while stirring and then the mixture is brought to reflux. The reaction is followed by titrating the amines with 0.1 N HCl using phenol red indicator. No isomelamine products are detectable by infrared analysis before 85% conversion. At 99+% conversion a maximum of 10% isomelamine products are present. At this point the reaction is cooled to 100° C. and neutralized with an equivalent amount of sodium hydroxide based upon the amount of acid catalyst remaining. The reactor is then closed and the excess 1,2-PA and the ethylene glycol is removed by distillation under vacuum at 150°–180° C. The isolated resin contains a maximum of 15% isomelamine compounds.

COMPARATIVE EXAMPLE B

The procedure of Example 2 is repeated except substituting ethanolamine for the 1-amino-2-propanol in equimolar amounts. At 80% conversion there is about 5% isomelamine, at 97% conversion 50% isomelamines, and after stripping off any unreacted ethanolamine there is greater than 55% isomelamines. In addition the product is darker in color than that of Example 2.

What is claimed is:

1. In a process for preparing hydroxy terminated melamine derivatives by reacting an alkanolamine with an amino-s-triazine compound of the formula

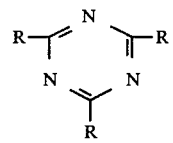

wherein each R is selected from the group consisting of alkyl ($C_1$–$C_{20}$), cycloalkyl ($C_5$–$C_8$), aryl ($C_6$–$C_{12}$), $NH_2$ and NHR' wherein R' is alkyl ($C_1$–$C_{20}$), cycloalkyl ($C_5$–$C_8$) or aryl ($C_6$–$C_{12}$) and at least one R is $NH_2$, the improvement comprising reducing the formation of isomelamine impurities by using an alkanolamine of the formula

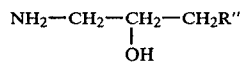

wherein R" is hydrogen, alkyl ($C_1$–$C_{20}$) or phenyl.

2. The process of claim 1 wherein each R is $NH_2$.

3. The process of claims 1 or 2 wherein R' is hydrogen.

4. The process of claim 1 wherein the reaction further contains an alkyl amine, arylamine, ether amine, alkyl diamine, or aryl diamine.

* * * * *